United States Patent
Geng et al.

(10) Patent No.: US 9,890,375 B2
(45) Date of Patent: Feb. 13, 2018

(54) ISOLATED OLIGONUCLEOTIDE AND USE THEREOF IN NUCLEIC ACID SEQUENCING

(71) Applicant: BGI SHENZHEN CO., LIMITED, Shenzhen (CN)

(72) Inventors: Chunyu Geng, Shenzhen (CN); Dennis G. Ballinger, Menlo Park, CA (US); Yanyan Zhang, Shenzhen (CN); Shujin Fu, Shenzhen (CN); Lingyu He, Shenzhen (CN); Wenwei Zhang, Shenzhen (CN); Hui Jiang, Shenzhen (CN)

(73) Assignee: BGI SHENZHEN CO., LIMITED, Shenzhen (CN)

( * ) Notice: Subject to any disclaimer, the term of this patent is extended or adjusted under 35 U.S.C. 154(b) by 0 days.

(21) Appl. No.: 15/510,877

(22) PCT Filed: Sep. 12, 2014

(86) PCT No.: PCT/CN2014/086418
§ 371 (c)(1),
(2) Date: Mar. 13, 2017

(87) PCT Pub. No.: WO2016/037358
PCT Pub. Date: Mar. 17, 2016

(65) Prior Publication Data
US 2017/0275609 A1 Sep. 28, 2017

(51) Int. Cl.
*C12Q 1/68* (2006.01)
*C12N 15/10* (2006.01)
(Continued)

(52) U.S. Cl.
CPC .......... *C12N 15/10* (2013.01); *B01J 19/0046* (2013.01); *C12Q 1/686* (2013.01); *C12Q 1/6806* (2013.01);
(Continued)

(58) Field of Classification Search
None
See application file for complete search history.

(56) References Cited

FOREIGN PATENT DOCUMENTS

| CN | 102296065 A | 12/2011 |
|---|---|---|
| CN | 103103624 A | 5/2013 |

(Continued)

OTHER PUBLICATIONS

Ukai et al. 2002 J Biotechnol. 97: 233-242.*
(Continued)

*Primary Examiner* — Suchira Pande
(74) *Attorney, Agent, or Firm* — Westman, Champlin & Koehler, P.A.; Z. Peter Sawicki

(57) ABSTRACT

Provided are an isolated oligonucleotide and a use thereof in nucleic acid sequencing, wherein the isolated oligonucleotide comprises a first strand, wherein the 5'-end nucleotide of the first strand has a phosphate group, and the 3'-end nucleotide of the first strand is a dideoxynucleotide, and a second strand, wherein the 5'-end nucleotide of the second strand does not have a phosphate group, and the 3'-end nucleotide of the second strand is a dideoxynucleotide, wherein the first strand is longer than the second strand in length, and a double-stranded structure is formed between the first strand and the second strand.

20 Claims, 5 Drawing Sheets

(51) Int. Cl.
  *B01J 19/00* (2006.01)
  *C40B 60/14* (2006.01)

(52) U.S. Cl.
  CPC .......... *C12Q 1/6811* (2013.01); *C12Q 1/6837* (2013.01); *C12Q 1/6853* (2013.01); *C40B 60/14* (2013.01); *B01J 2219/00529* (2013.01); *C12Q 2565/537* (2013.01)

(56) References Cited

FOREIGN PATENT DOCUMENTS

| WO | 9746704 | A1 | 12/1997 |
| WO | 2007076420 | A2 | 7/2007 |
| WO | 2007140417 | A2 | 12/2007 |
| WO | 2008070375 | A2 | 12/2007 |
| WO | 2008070352 | A2 | 6/2008 |
| WO | 2009061840 | A1 | 5/2009 |
| WO | 2009076238 | A2 | 6/2009 |
| WO | 2012037876 | A1 | 3/2012 |
| WO | 2012037880 | A1 | 3/2012 |
| WO | 2012079486 | A1 | 6/2012 |
| WO | 2015117040 | A1 | 8/2015 |

OTHER PUBLICATIONS

International Search Report issued for PCT/CN2014/086418, dated Jun. 15, 2015.
Written Opinion of the International Searching Authority issued for PCT/CN2014/086418, dated Jun. 15, 2015.
Ukai H., et al. "A new technique to prevent self-ligation of DNA" Journal of Biotechnology vol. 97, Dec. 31, 2002, pp. 233-242.
Office action from EPO for EP application 14901591 dated Nov. 14, 2017.

* cited by examiner

ISOLATED OLIGONUCLEOTIDE AND USE THEREOF IN NUCLEIC ACID SEQUENCING

CROSS-REFERENCE TO RELATED APPLICATION

This application is the U.S. national phase of PCT Application No. PCT/CN2014/086418 filed on Sep. 12, 2014, the entire content of which is incorporated herein by reference.

FIELD

The present disclosure relates to the field of biotechnology, specifically to isolated oligonucleotide and use thereof in nucleic acid sequencing, more particularly to an isolated oligonucleotide, a kit, a method for adding adaptors to terminals of a double-stranded fragment, a method of constructing a library for sequencing a double-stranded DNA fragment and a method for sequencing nucleic acids.

BACKGROUND

High throughout sequencing has become one basis in the fields of molecular biology, biotechnology and medical science. It has gradually been innovating a rapid, accurate and low-cost method for determining gene expression level and nucleotide sequence in the last several years. As it has getting matured for the Next-Generation high-throughput sequencing technology based on Sequencing by Synthesis, various major sequencing companies have paid their attention to develop new sequencing product, shorten sequence process and lower sequencing cost. Currently available sequencing product based on the Next-Generation sequencing technology includes whole genome resequencing, whole transcriptome resequencing and microRNA sequencing, and etc. In particular, a target sequence capturing and sequencing technology derived from the Next-Generation sequencing technology and microarray technology allows for utilizing a large amount of oligonucleotide probes to complementary combine with a specific region on genome, so as to enrich the specific region, which is subsequently sequenced by the Next-Generation sequencing technology, such that whole exon exome sequencing (WES) for human is achieved. Such the whole exon exome sequencing (WES) has obvious advantages as compared to the whole genome sequencing due to low volume of data analysis.

However, it still needs to improve related technology for sequencing nucleotide sequences.

SUMMARY

The present disclosure seeks to solve at least one of the technical problems in the related art to some extent.

First, it should be noted that the present disclosure is accomplished by inventors based on the following discoveries.

At present, Complete Genomics (sometimes referred to as "CG" in the context) has already owned a set of Next-Generation sequencing technology, which is developed independently and adapted for whole genome sequencing for human. A process for constructing a library mainly includes the following steps: genomic DNA fragmentation, adaptor ligation for the first time, double-stranded DNA cyclization followed by digestion, adaptor ligation for the second time, and single-stranded DNA isolation followed by cyclization, in which two steps of adaptor ligation is very important for the whole process for constructing the library. After ligated to a DNA fragment at two terminals, the adaptor (a DNA sequence) can be recognized as an initiation site for sequencing, allowing instrument to read sequence information thereafter.

To ensure acquired sequencing information to be analyzed easily, it is required to ligate two different adaptors at two ends (the 5'-end and the 3'-end) of one DNA fragment. Subsequently, further to achieve the ligation with a specific direction and avoid interconnection between adaptors, an adaptor with cohesive ends is used. However, it is difficult to avoid the adaptors with cohesive ends from interconnection. Complete Genomics constructs the library for sequencing by ligating the adaptor at two ends in several steps, including: adaptor ligation at one end of a DNA fragment; denature, annealing and extension; adaptor ligation at the other one end of the DNA fragment; nick translation, and polymerase chain reaction. Accordingly, overall sequencing cost is high due to expensive reagents required for multiple extensions, and sequencing efficiency is low because of multiple steps of purification and recovery between individual steps. Moreover, such a protocol in the current available process for constructing the library requires two times of adaptor ligation. Therefore, the present disclosure provides in embodiments a method for ligating different adaptors to a DNA fragment at two terminals.

In a first aspect, the present disclosure provides in embodiments an isolated oligonucleotide including a first strand and a second strand, in which a first terminal nucleotide at the 5'-end of the first strand has a phosphate group, and a second terminal nucleotide at the 3'-end of the first strand is dideoxynucleotide; and a third terminal nucleotide at the 5'-end of the second strand has no phosphate group, and a fourth terminal nucleotide at the 3'-end of the second strand is dideoxynucleotide, in which the first strand is of a length longer than that of the second strand, and a double-stranded structure is formed between the first strand and the second strand. This oligonucleotide cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an isolated oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction.

In a second aspect, the present disclosure provides in embodiments a kit. In some embodiments, the kit includes: a first adaptor and a second adaptor each being the isolated oligonucleotide described above, in which the first adaptor is different from the second adaptor. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an kit may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the kit, which is no more described in detail here.

In a third aspect, the present disclosure provides in embodiments a method for adding adaptors, including a first adaptor and a second adaptor, to a double-stranded DNA fragment respectively at two terminals. In some embodiments of the present disclosure, the double-stranded DNA fragment includes two terminals, each of which includes paired blunt ends without any phosphate group. In some embodiments, the method includes ligating the first adaptor and the second adaptor to the double-stranded DNA fragment respectively at two terminals, to obtain a first ligated product, in which the first adaptor is different from the second adaptor; and the first adaptor and the second adaptor each are the isolated oligonucleotide described above; replacing a second strand of the first adaptor by a first single-stranded DNA and replacing a second strand of the second adaptor by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure; connecting the first single-stranded DNA and the second single-stranded DNA to the double-stranded DNA fragment respectively at two terminals to obtain a second ligated product; and amplifying the second ligated product with a first primer and a second primer to obtain an amplified product, in which the amplified product is a DNA fragment ligated with the first and second adaptors respectively at two terminals, the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals.

In a fourth aspect, the present disclosure provides in embodiments a method of constructing a library for sequencing a double-stranded DNA fragment with two terminals, each of which includes paired blunt ends without any phosphate group. In some embodiments, the method includes: ligating the first adaptor and the second adaptor to the double-stranded DNA respectively at two terminals by the method for adding adaptors described above, to obtain a DNA fragment ligated with the first and second adaptors respectively at two terminals; separating the DNA fragment ligated with the first and second adaptors respectively at two terminals into single-stranded DNA fragments; and cyclizing the single-stranded DNA fragment to obtain a single-stranded DNA loop, in which the single-stranded DNA loop constitutes the library for sequencing the double-stranded DNA fragment with two terminals. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library for sequencing may be obtained efficiently, e.g. a library for CG sequencing platform.

In a fifth aspect, the present disclosure provides in embodiments a method for sequencing nucleic acids. In some embodiments, the method includes: constructing a library by the method of constructing the library for sequencing the double-stranded DNA fragment described above; and sequencing the library. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform, thus further improving sequencing efficiency, and reducing sequencing cost.

In a sixth aspect, the present disclosure provides in embodiments a device for adding adaptors, including a first adaptor and a second adaptor, to a double-stranded DNA fragment respectively at two terminals, each of which includes paired blunt ends without any phosphate group. In some embodiments, the device includes: a first ligating unit configured to ligate the first adaptor and the second adaptor to the double-stranded DNA fragment respectively at two terminals, to obtain a first ligated product, in which the first adaptor is different from the second adaptor, and the first adaptor and the second adaptor each are the isolated oligonucleotide described above; a replacing unit configured to replace a second strand of the first adaptor by a first single-stranded DNA and replace a second strand of the second adaptor by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure; a second ligating unit configured to connect the first single-stranded DNA and the second single-stranded DNA respectively to the double-stranded DNA fragment respectively at two terminals, to obtain a second ligated product, and an amplifying unit configured to amplify the second ligated product with a first primer and a second primer to obtain an amplified product, in which the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals.

In a seventh aspect, the present disclosure provides in embodiments a device of constructing a library for sequencing a double-stranded DNA fragment with two terminals, each of which includes paired blunt ends without any phosphate group. In some embodiments, the device includes: the device for adding adaptors configured to ligate the first adaptor and the second adaptor to the double-stranded DNA respectively at two terminals, to obtain a DNA fragment ligated with the first and second adaptors respectively at two terminals; a single-stranded DNA fragment isolating device configured to isolate a single-stranded DNA fragment from the DNA fragment ligated with the first and second adaptors respectively at two terminals; and a cyclizing device configured to cyclize the single-stranded DNA fragment to obtain a single-stranded DNA loop, in which the single-stranded DNA loop constitutes the library for sequencing the double-stranded DNA fragment with two terminals. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform.

In an eighth aspect, the present disclosure provides in embodiments a system for sequencing nucleic acids. In some embodiments, the system includes: the device of constructing the library for sequencing the double-stranded DNA fragment with two terminals described above; and a sequencing device configured to sequence the library. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the system, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform, thus further improving sequencing efficiency, and reducing sequencing cost.

In a ninth aspect, the present disclosure provides in embodiments a device of constructing a library for sequencing genomic DNA. In some embodiments, the device includes: a first unit configured to fragment the genomic DNA sample to obtain a fragmentation product; a second unit configured to dephosphorylate the fragmentation product to obtain a dephosphorylated fragmentation product; a third unit configured to end-repair the dephosphorylated fragmentation product to obtain the double-stranded DNA fragment; a fourth unit configured to ligate the first adaptor and the second adaptor to the double-stranded DNA fragment respectively at two terminals, to obtain a first ligated product, in which the first adaptor is different from the second adaptor, and the first adaptor and the second adaptor each are the isolated oligonucleotide described above; a fifth unit configured to replace a second strand of the first adaptor by a first single-stranded DNA and replace a second strand of the second adaptor by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure; a sixth unit configured to connect the first single-stranded DNA and the second single-stranded DNA to the double-stranded DNA fragment respectively at two terminals, to obtain a second ligated product; a seventh unit configured to amplify the second ligated product with a first primer and a second primer to obtain an amplified product, in which the amplified product is a DNA fragment ligated with the first and second adaptors respectively at two terminals, the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA; an eighth unit configured to isolate a single-stranded DNA fragment from the DNA fragment ligated with the first and second adaptors respectively at two terminals; and a ninth unit configured to cyclize the single-stranded DNA fragment to obtain a single-stranded DNA loop, in which the single-stranded DNA loop constitutes the library for sequencing the genomic DNA. As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Figure 1:
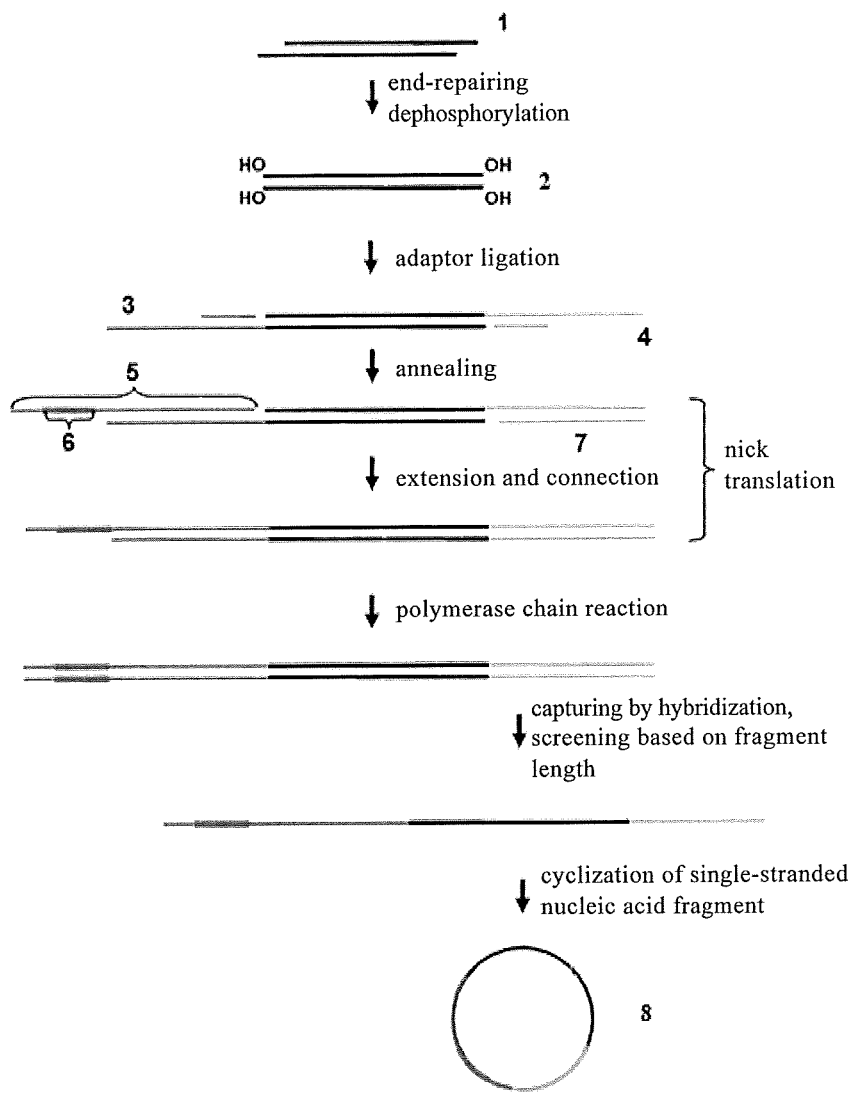
FIG. 1 is a flow chart showing a process of library construction in an embodiment of the present disclosure, in which 1 refers to a fragmented DNA fragment, 2 refers to a dephosphorylated and end-repaired DNA fragment (each end is hydroxyl), 3 refers to an adaptor A, 4 refers to an adaptor B, 5 refers to a single-stranded nucleic acid C, 6 refers to a tag sequence of the single-stranded nucleic acid C, 7 refers to a single-stranded nucleic acid D and 8 refers to a cyclized single-stranded nucleic acid which is a final product.

Reference will be made in detail to embodiments of the present disclosure. The embodiments described herein with reference to drawings are explanatory, illustrative, and used to generally understand the present disclosure. The embodiments shall not be construed to limit the present disclosure.

In addition, terms such as "first" and "second" are used herein for purposes of description and are not intended to indicate or imply relative importance or significance. Thus, features restricted with "first" and "second" may explicitly or implicitly include one or more of the features. Furthermore, in the description of the present disclosure, unless otherwise stated, the term "a plurality of" refers to two or more. Besides, in the present disclosure, wordings "ligate", "ligating", "ligated" or "ligation" mean that two single-stranded nucleic acid molecules form one longer single-stranded nucleic acid molecule directly nucleotide by nucleotide because of the presence of the phosphorylation group at the 5'-end of one single-stranded nucleic acid molecule; whereas wordings "connect", "connecting", "connected" or "connection" indicate that two single-stranded nucleic acid molecules form one longer single-stranded nucleic acid molecule indirectly by means of other reaction, such as nick translation followed by ligation.

Isolated Oligonucleotide and Kit

In a first aspect, the present disclosure provides in embodiments an isolated oligonucleotide. In an embodiment of the present disclosure, the isolated oligonucleotide includes: a first strand and a second strand, in which a first terminal nucleotide at the 5'-end of the first strand has a phosphate group, and a second terminal nucleotide at the 3'-end of the first strand is dideoxynucleotide; and a third terminal nucleotide at the 5'-end of the second strand has no phosphate group, and a fourth terminal nucleotide at the 3'-end of the second strand is dideoxynucleotide, in which the first strand is of a length longer than that of the second strand, and a double-stranded structure is formed between the first strand and the second strand. The oligonucleotide cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such a kit may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction.

In an embodiment of the present disclosure, the number of nucleotides mismatched between the second strand and the first strand is no more than 3, thus further improving the ligating efficiency and reducing economic and time cost for library construction.

In an embodiment of the present disclosure, the isolated oligonucleotide includes a first overhang, located at the 3'-end of the first strand; and optionally, a second overhang, located at the 5'-end of the second strand, thus further improving the ligating efficiency and reducing economic and time cost for library construction.

In an embodiment of the present disclosure, the first overhang is of a length longer than that of the second overhang, thus further improving the ligating efficiency and reducing economic and time cost for library construction.

In an embodiment of the present disclosure, the length of the first overhang is about 6 nt to about 12 nt, thus further improving the ligating efficiency and reducing economic and time cost for library construction.

In an embodiment of the present disclosure, the length of the second overhang is 0 nt to 4 nt, thus further improving the ligating efficiency and reducing economic and time cost for library construction.

In an embodiment of the present disclosure, the first and second strands are both DNAs.

In an embodiment of the present disclosure, the length of the first strand is about 20 nt to about 25 nt, thus further improving the ligating efficiency and reducing economic and time cost for library construction.

In an embodiment of the present disclosure, the length of the second strand is about 10 nt to about 15 nt, thus further improving the ligating efficiency and reducing economic and time cost for library construction.

In an embodiment of the present disclosure, the first strand has a sequence of 5'GGCTCCGTCGAAGC-CCGACGC3' (SEQ ID NO: 1), and the second strand has a sequence of 5'CTTCGACGGAGCC3' (SEQ ID NO: 2); or the first strand has a sequence of 5'ACGTCGGGGC-CAAGCGGTCGTC3' (SEQ ID NO: 3), and the second strand has a sequence of 5'TTGGCCCCGGCTT3' (SEQ ID NO: 4), thus further improving the ligating efficiency and reducing economic and time cost for library construction.

In a second aspect, the present disclosure provides in embodiments a kit. In an embodiment of the present disclosure, the kit includes a first adaptor and a second adaptor each being the isolated oligonucleotide described above, in which the first adaptor is different from the second adaptor.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such a kit may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the kit, which is no more described in detail here.

In an embodiment of the present disclosure, the kit further includes a first single-stranded DNA capable of pairing with a first strand of the first adaptor to form a first double-stranded structure; and a second single-stranded DNA capable of pairing with a first strand of the second adaptor to form a second double-stranded structure. Therefore, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals.

In an embodiment of the present disclosure, the first double-stranded structure is of a length longer than that of a third double-stranded structure formed with the first strand of the first adaptor and a second strand of the first adaptor; and the second double-stranded structure is of a length longer than that of a fourth double-stranded structure formed with the first strand of the second adaptor and a second strand of the second adaptor, thus further improving the ligating efficiency and reducing economic and time cost for library construction.

In an embodiment of the present disclosure, the kit further includes a first primer being the same as one of the first single-stranded DNA and the second single-stranded DNA; and a second primer having additional biotin at the 5'-end as compared to the other one of the first single-stranded DNA and the second single-stranded DNA, thus further improving the ligating efficiency and reducing economic and time cost for library construction. Moreover, the single-stranded nucleic acid molecule may be isolated effectively by an agent capable of specifically binding with a biotin and may be further used to construct a library for CG sequencing platform.

In an embodiment of the present disclosure, the first strand of the first adaptor has a sequence of 5'GGCTC-CGTCGAAGCCCGACGC3' (SEQ ID NO:1); a second strand of the first adaptor has a sequence of 5'CTTCGACG-GAGCC3' (SEQ ID NO:2); the first strand of the second adaptor has a sequence of 5'ACGTCGGGGCCAAGCG-GTCGTC3' (SEQ ID NO:3); a second strand of the second adaptor has a sequence of 5'TTGGCCCCGGCTT3' (SEQ ID NO:4); the first single-stranded DNA has a sequence of 5'AGACAAGCTC(N)$_m$GATCGGGCTTCGACGGAG3', in which (N)$_m$ represents a tag sequence being of a length of m nucleotides, where m is an integer ranging from 4 to 10, and N represents adenine (A), thymine (T), guanine (G) or cytosine (C); and the second single-stranded DNA has a sequence of 5'TCCTAAGACCGCTTGGCCCCG3' (SEQ ID NO:5), thus further improving the ligating efficiency and reducing economic and time cost for library construction. Moreover, the single-stranded nucleic acid molecule may be isolated effectively by an agent capable of specifically binding with a biotin and may be further used to construct a library for CG sequencing platform.

Use of the Isolated Oligonucleotide in Sequencing Nucleic Acids

Figure 4:
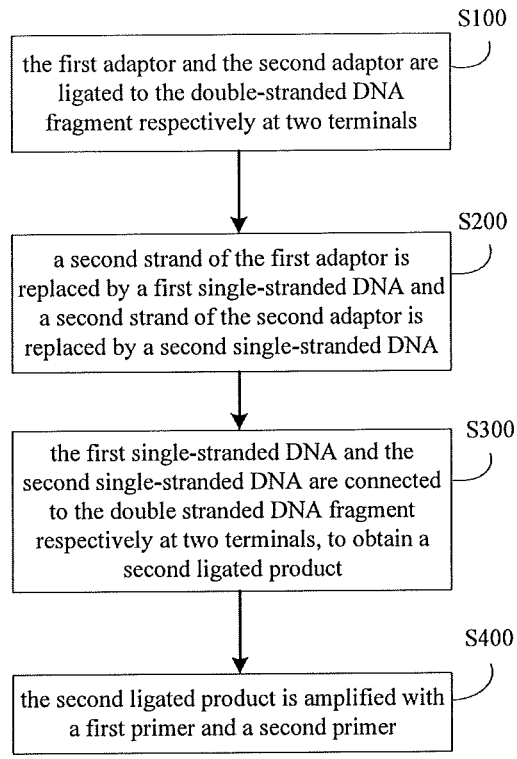
FIG. 4 is a flow chart showing a method for adding adaptors to a double-stranded DNA fragment respectively at two terminals in an embodiment of the present disclosure.

In a third aspect, the present disclosure provides in embodiments a method for adding adaptors, including a first adaptor and a second adaptor, to a double-stranded DNA fragment respectively at two terminals, each of which includes paired blunt ends without any phosphate group. With reference to FIG. 4, in an embodiment, the method includes the following steps S100 to S400.

S100: The First Adaptor and the Second Adaptor are Ligated to the Double-Stranded DNA Fragment Respectively at Two Terminals.

The first adaptor and the second adaptor are ligated to the double-stranded DNA fragment respectively at two terminals, to obtain a first ligated product, in which the first adaptor is different from the second adaptor, and the first adaptor and the second adaptor each are the isolated oligonucleotide described above.

In an embodiment of the present disclosure, the first adaptor and the second adaptor are ligated to the double-stranded DNA fragment respectively at two terminals in one step.

In an embodiment of the present disclosure, the double-stranded DNA fragment is obtained by the following steps: fragmenting a DNA sample to obtain a fragmentation product; dephosphorylating the fragmentation product to obtain a dephosphorylated fragmentation product; and end-repairing the dephosphorylated fragmentation product to obtain the double-stranded DNA fragment, thereby effectively obtaining the DNA fragment suitable for library construction.

In an embodiment of the present disclosure, the DNA sample is at least part of genomic DNA or an RNA reverse transcription product, such that the library for sequencing the genomic DNA or RNA can be effectively constructed.

S200: A Second Strand of the First Adaptor is Replaced by a First Single-Stranded DNA and a Second Strand of the Second Adaptor is Replaced by a Second Single-Stranded DNA.

A second strand of the first adaptor is replaced by a first single-stranded DNA and a second strand of the second adaptor is replaced by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure.

In an embodiment of the present disclosure, the first double-stranded structure is of a length longer than that of a third double-stranded structure formed with the first strand of the first adaptor and a second strand of the first adaptor; and the second double-stranded structure is of a length longer than that of a fourth double-stranded structure formed with the first strand of the second adaptor and a second strand of the second adaptor, thus further improving sequencing efficiency, and reducing sequencing cost.

In an embodiment of the present disclosure, the first strand of the first adaptor has a sequence of 5'GGCTC-CGTCGAAGCCCGACGC3' (SEQ ID NO:1); a second strand of the first adaptor has a sequence of 5'CTTCGACG-GAGCC3' (SEQ ID NO:2); the first strand of the second adaptor has a sequence of 5'ACGTCGGGGCCAAGCG-GTCGTC3' (SEQ ID NO:3); a second strand of the second adaptor has a sequence of 5' TTGGCCCCGGCTT3' (SEQ ID NO:4); the first single-stranded DNA has a sequence of 5'AGACAAGCTC(N)$_m$GATCGGGCTTCGACGGAG3', in which (N)$_m$ represents a tag sequence being of a length of m nucleotides, where m is an integer ranging from 4 to 10, and N represents adenine (A), thymine (T), guanine (G) or cytosine (C); and the second single-stranded DNA has a sequence of 5'TCCTAAGACCGCTTGGCCCCG3' (SEQ ID NO:5), thereby further improving sequencing efficiency, and reducing sequencing cost. Moreover, the single-stranded nucleic acid molecule may be isolated effectively by an agent capable of specifically binding with a biotin and may be further used to construct a library for CG sequencing platform.

In an embodiment of the present disclosure, the second strand of the first adaptor and the second strand of the second adaptor are replaced respectively by the first single-stranded DNA and the second single-stranded DNA by means of thermal denaturation-annealing. In a specific embodiment of the present disclosure, the thermal denaturation is performed at about 60° C., thereby further improving the ligating efficiency and reducing economic and time cost for library construction.

S300: The First Single-Stranded DNA and the Second Single-Stranded DNA are Connected to the Double-Stranded DNA Fragment Respectively at Two Terminals.

The first single-stranded DNA and the second single-stranded DNA are connected to the double-stranded DNA fragment respectively at two terminals, to obtain a second ligated product.

In an embodiment of the present disclosure, the first single-stranded DNA and the second stranded DNA are connected to the double-stranded DNA fragment respectively at two terminals by means of nick translation.

S400: The Second Ligated Product is Amplified with a First Primer and a Second Primer.

The second ligated product is amplified with a first primer and a second primer to obtain an amplified product, in which the amplified product is a DNA fragment ligated with the first and second adaptors respectively at two terminals, the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals.

In a fourth aspect, the present disclosure provides in embodiments a method of constructing a library for sequencing a double-stranded DNA fragment with two terminals, each of which includes paired blunt ends without any phosphate group. In an embodiment of the present disclosure, the method includes the following steps.

Firstly, the first adaptor and the second adaptor are ligated to the double-stranded DNA respectively at two terminals by the method for adding adaptors described above, to obtain a DNA fragment ligated with the first and second adaptors respectively at two terminals.

Secondly, a single-stranded DNA fragment is isolated from the DNA fragment ligated with the first and second adaptors respectively at two terminals. In an embodiment of the present disclosure, separating the DNA fragment ligated with the first and second adaptors respectively at two terminals into single-stranded DNA fragments further includes: contacting the DNA fragment ligated with the first and second adaptors respectively at two terminals with magnetic beads to form a magnetic bead-DNA complex, in which the magnetic bead is coated with streptavidin; and exposing the magnetic bead-DNA complex to a solution being of a pH value higher than 7 to obtain the single-stranded DNA fragment, thereby effectively isolating the single-stranded DNA fragment, so as to improve efficiency of library construction and reduce cost for library construction. In an embodiment of the present disclosure, the solution being of the pH value higher than 7 is a sodium hydroxide solution. In an embodiment of the present disclosure, the sodium hydroxide solution is of a concentration about 0.5 M to 2 M. In an embodiment of the present disclosure, the sodium hydroxide solution is of a concentration about 1 M. In an embodiment of the present disclosure, the single-stranded DNA fragment is isolated from the DNA fragment ligated with the first and second adaptors respectively at two terminals which has been screened in advance, thereby constructing the library for sequencing a predetermined region. In an embodiment of the present disclosure, the DNA fragment ligated with the first and second adaptors respectively at two terminals is screened by means of contact with a probe, in which the probe is specific to a predetermined sequence. In an embodiment of the present disclosure, the predetermined sequence includes at least one exon. In an embodiment of the present disclosure, the probe is provided in a microchip array form. Therefore, the single-stranded DNA fragment may be cyclized effectively.

Afterwards, the single-stranded DNA fragment is cyclized to obtain a single-stranded DNA loop, in which the single-stranded DNA loop constitutes the library for sequencing the double-stranded DNA fragment with two terminals. In an embodiment of the present disclosure, the single-stranded DNA fragment is cyclized with a single-stranded nucleic acid molecule, in which the single-stranded nucleic acid molecule includes a first region and a second region, the first region is capable of pairing with terminal nucleotides at the 5'-end and the 3'-end of the single-stranded DNA fragment, and the second region is capable of pairing with terminal nucleotides at the 5'-end or the 3'-end of the single-stranded DNA fragment, thereby further improving cyclizing efficiency. In an embodiment of the present disclosure, the first region is adjacent connected to the second region. In an embodiment of the present disclosure, the first region has a sequence of 5'TCGAGCTTGTCT3' (SEQ ID NO:6); and the second region has a sequence of 5'TCCTAAGACCGC3' (SEQ ID NO:7).

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the fast single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform.

In a fifth aspect, the present disclosure provides in embodiments a method for sequencing nucleic acids. In some embodiments, the method includes: constructing a library by the method of constructing the library for sequencing the double-stranded DNA fragment; and sequencing the library. In an embodiment of the present disclosure, the library was sequenced on a Complete Genomics (CG) sequencing platform.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the method, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform, thus further improving sequencing efficiency, and reducing sequencing cost.

Figure 5:
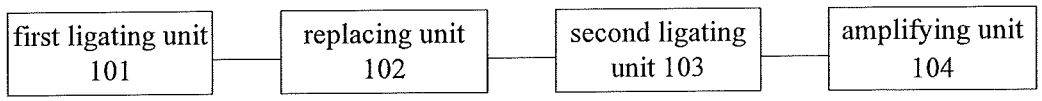
FIG. 5 is a schematic diagram showing a device for adding adaptors to a double-stranded DNA fragment respectively at two terminals in an embodiment of the present disclosure.

In a sixth aspect, the present disclosure provides in embodiments a device for adding adaptors, including a first adaptor and a second adaptor, to a double-stranded DNA fragment respectively at two terminals, each of which includes paired blunt ends without any phosphate group. With reference to FIG. 5, in some embodiments, the device 100 includes: a first ligating unit 101, a replacing unit 102, a second ligating unit 103 and an amplifying unit 104.

The first ligating unit 101 is configured to ligate the first adaptor and the second adaptor to the double-stranded DNA fragment respectively at two terminals, to obtain a first ligated product, in which the first adaptor is different from the second adaptor, and the first adaptor and the second adaptor each are the isolated oligonucleotide described above. In an embodiment of the present disclosure, the first adaptor and the second adaptor are ligated to the double-stranded DNA fragment respectively at two terminals in one step.

The replacing unit 102 is configured to replace a second strand of the first adaptor by a first single-stranded DNA and replace a second strand of the second adaptor by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure. In an embodiment of the present disclosure, the first double-stranded structure is of a length longer than that of a third double-stranded structure formed with the first strand of the first adaptor and a second strand of the first adaptor; and the second double-stranded structure is of a length longer than that of a fourth double-stranded structure formed with the first strand of the second adaptor and a second strand of the second adaptor, thus further improving the ligating efficiency and reducing economic and time cost for library construction. In an embodiment of the present disclosure, the first strand of the first adaptor has a sequence of 5'GGCTCCGTCGAAGCCCGACGC3' (SEQ ID NO:1); a second strand of the first adaptor has a sequence of 5'CTTCGACGGAGCC3' (SEQ ID NO:2); the first strand of the second adaptor has a sequence of 5'ACGTCGGGGCCAAGCGGTCGTC3' (SEQ ID NO:3); a second strand of the second adaptor has a sequence of 5'TTGGCCCCGGCTT3' (SEQ ID NO:4); the first single-stranded DNA has a sequence of 5'AGACAAGCTC(N)$_m$GATCGGGCTTCGACGGAG3', in which (N)$_m$ represents a tag sequence being of a length of m nucleotides, where m is an integer ranging from 4 to 10, and N represents adenine (A), thymine (T), guanine (G) or cytosine (C); and the second single-stranded DNA has a sequence of 5'TCCTAAGACCGCTTGGCCCCG3' (SEQ ID NO:5), thus further improving the ligating efficiency and reducing economic and time cost for library construction. Moreover, the single-stranded nucleic acid molecule may be isolated effectively by an agent capable of specifically binding with a biotin and may be further used to construct a library for CG sequencing platform.

In an embodiment of the present disclosure, the replacing unit 102 is configured to replace the second strand of the first adaptor and the second strand of the second adaptor respectively by the first single-stranded DNA and the second single-stranded DNA by means of thermal denaturation-annealing. In an embodiment of the present disclosure, the thermal denaturation is performed at about 60° C., thus further improving the ligating efficiency and reducing economic and time cost for library construction.

The second ligating unit 103 is configured to connect the first single-stranded DNA and the second single-stranded DNA to the double-stranded DNA fragment respectively at two terminals, to obtain a second ligated product. In an embodiment of the present disclosure, the second ligating unit 103 is configured to connect the first single-stranded DNA and the second stranded DNA to the double-stranded DNA fragment respectively at two terminals by means of nick translation.

The amplifying unit 104 is configured to amplify the second ligated product with a first primer and a second primer to obtain an amplified product, in which the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA.

In an embodiment of the present disclosure, the device further includes a double-stranded DNA fragment obtaining unit (not shown in drawings), and the double-stranded DNA fragment obtaining unit includes: a fragmenting assembly configured to fragment a DNA sample to obtain a fragmentation product; a dephosphorylating assembly configured to dephosphorylate the fragmentation product to obtain a dephosphorylated fragmentation product; and an end-repairing assembly configured to end-repair the dephosphorylated fragmentation product to obtain the double-stranded DNA fragment, thus effectively obtaining the double-stranded DNA fragment for library construction.

In an embodiment of the present disclosure, the double-stranded DNA fragment obtaining unit further includes: a genomic DNA extracting assembly configured to extract genomic DNA from a biological sample; and/or a reverse transcription assembly configured to subject a RNA sample to reverse transcription to obtain a reverse transcription product, in which at least part of genomic DNA and/or the reverse transcription product constituent(s) the DNA sample, thereby effectively constructing the library for sequencing genomic DNA or RNA.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals.

Figure 6:
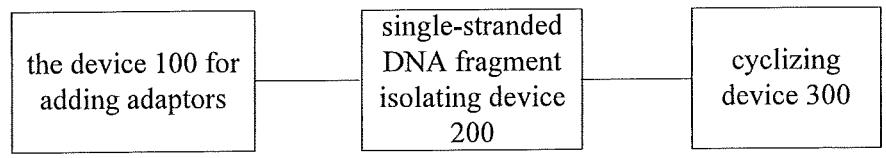
FIG. 6 is a schematic diagram showing a device of constructing a library for sequencing a double-stranded DNA fragment in an embodiment of the present disclosure.

In a seventh aspect, the present disclosure provides in embodiments a device of constructing a library for sequencing a double-stranded DNA fragment with two terminals, each of which includes paired blunt ends without any phosphate group. With reference to FIG. 6, in some embodiments, the device includes: the device 100 for adding adaptors, a single-stranded DNA fragment isolating device 200 and a cyclizing device 300.

The device 100 for adding adaptors is configured to ligate the first adaptor and the second adaptor to the double-stranded DNA respectively at two terminals, to obtain a DNA fragment ligated with the first and second adaptors respectively at two terminals. The single-stranded DNA fragment isolating device 200 is configured to isolate a single-stranded DNA from the DNA fragment ligated with the first and second adaptors respectively at two terminals. The cyclizing device 300 is configured to cyclize the single-stranded DNA fragment to obtain a single-stranded DNA loop, in which the single-stranded DNA loop constitutes the library for sequencing the double-stranded DNA fragment with two terminals.

In an embodiment of the present disclosure, the single-stranded DNA fragment isolating device 200 further includes: a capturing unit provided with magnetic beads, and configured to contact the DNA fragment ligated with the first and second adaptors respectively at two terminals with magnetic beads, to form a magnetic bead-DNA complex, in which the magnetic bead is coated with streptavidin; and a lysing unit provided with a solution being of a PH value higher than 7, and configured to expose the magnetic bead-DNA complex to the solution, to obtain the single-stranded DNA fragment, thereby effectively isolating the single-stranded DNA fragment, so as to improve efficiency of library construction and reduce cost for library construction. In an embodiment of the present disclosure, the solution being of the pH value higher than 7 is a sodium hydroxide solution. In an embodiment of the present disclosure, the sodium hydroxide solution is of a concentration about 0.5 M to 2 M. In another embodiment of the present disclosure, the sodium hydroxide solution is of a concentration about 1 M.

In an embodiment of the present disclosure, the device further includes a screening device (not shown in drawings). The screening device is configured to screen the DNA fragment ligated with the first and second adaptors respectively at two terminals, from which the single-stranded DNA fragment is isolated thereafter. In an embodiment of the present disclosure, the screening device is provided with a probe, in which the probe is specific to a predetermined sequence. In an embodiment of the present disclosure, the predetermined sequence includes at least one exon. In an embodiment of the present disclosure, the probe is provided in a microchip array form.

In an embodiment of the present disclosure, the cyclizing device 300 is provided with a single-stranded nucleic acid molecule, in which the single-stranded nucleic acid molecule includes a first region and a second region, the first region is capable of pairing with terminal nucleotides at the 5'-end and the 3'-end of the single-stranded DNA fragment, and the second region is capable of pairing with terminal nucleotides at the 5'-end or the 3'-end of the single-stranded DNA fragment. In an embodiment of the present disclosure, the first region is adjacent connected to the second region. In an embodiment of the present disclosure, the first region has a sequence of 5'TCGAGCTTGTCT3' (SEQ ID NO:6), and the second region has a sequence of 5'TCCTAAGACCGC3' (SEQ ID NO:7). Therefore, the single-stranded DNA fragment may be cyclized effectively.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform.

Figure 7:
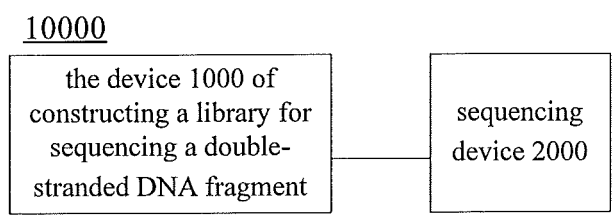
FIG. 7 is a schematic diagram showing a system for sequencing nucleic acids in an embodiment of the present disclosure.

In an eighth aspect, the present disclosure provides in embodiments a system for sequencing nucleic acids. With reference to FIG. 7, in some embodiments, the system 10000 includes: the device 1000 of constructing the library for sequencing the double-stranded DNA fragment described above; and a sequencing device 2000 configured to sequence the library. In an embodiment of the present disclosure, the sequencing device 2000 is a CG sequencing platform.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor for library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the system, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform, thus further improving sequencing efficiency, and reducing sequencing cost.

In a ninth aspect, the present disclosure provides in embodiments a device of constructing a library for sequencing genomic DNA. In some embodiments, the device includes: a first unit configured to fragment the genomic DNA sample to obtain a fragmentation product; a second unit configured to dephosphorylate the fragmentation product to obtain a dephosphorylated fragmentation product; a third unit configured to end-repair the dephosphorylated fragmentation product to obtain the double-stranded DNA fragment; a fourth unit configured to ligate the first adaptor and the second adaptor to the double-stranded DNA fragment respectively at two terminals, to obtain a first ligated product, in which the first adaptor is different from the second adaptor, and the first adaptor and the second adaptor each are the isolated oligonucleotide described above; a fifth unit configured to replace a second strand of the first adaptor by a first single-stranded DNA and replace a second strand of the second adaptor by a second single-stranded DNA, in which the first single-stranded DNA is capable of specifically pairing with a first strand of the first adaptor to form a first double-stranded structure, and the second single-stranded DNA is capable of specifically pairing with a first strand of the second adaptor to form a second double-stranded structure; a sixth unit configured to connect the first single-stranded DNA and the second single-stranded DNA to the double-stranded DNA fragment respectively at two terminals, to obtain a second ligated product; a seventh unit configured to amplify the second ligated product with a first primer and a second primer to obtain an amplified product, in which the amplified product is a DNA fragment ligated with the first and second adaptors respectively at two terminals, the first primer contains the same sequence as one of the first single-stranded DNA and the second single-stranded DNA, and the second primer contains the same sequence as the other one of the first single-stranded DNA and the second single-stranded DNA and contains additional biotin at the 5'-end as compared to the other one of the first single-stranded DNA and the second single-stranded DNA; an eighth unit configured to isolate a single-stranded DNA fragment from the DNA fragment ligated with the first and second adaptors respectively at two terminals; and a ninth configured to cyclize the single-stranded DNA fragment to obtain a single-stranded DNA loop, in which the single-stranded DNA loop constitutes the library for sequencing the genomic DNA.

As described above, the oligonucleotide according to embodiments of the present disclosure cannot be connected with other nucleic acid fragments at the 3'-ends of the first and second strands due to the dideoxynucleotide, or at the 5'-end of the second strand without the phosphate group, thereby avoiding oligonucleotides from connecting to each other. Accordingly, such an oligonucleotide may be used as an adaptor library construction, thereby ligating different adaptors to nucleic acid fragment respectively at two terminals during library construction, which not only avoids the adaptors from connecting to each other, but also improves ligating efficiency, as well as reduces economic and time cost for library construction. Descriptions as to features and advantages of the isolated oligonucleotide according to embodiments of the present disclosure are also applicable to the device, which is no more described in detail here. In addition, the second strand of the first adaptor and the second strand of the second adaptor are replaced respectively by the first single-stranded DNA and the second single-stranded DNA during library construction, so that a more stable structure is formed with the first strand of the first adaptor and the first strand of the second adaptor. Furthermore, the second ligated product is amplified by polymerase chain reaction (PCR) with the first single-stranded DNA and the second single-stranded DNA used as primers, thereby forming a DNA fragment with stable adaptors at both terminals. Subsequently, a single-stranded DNA fragment is isolated and cyclized, so that the library may be obtained efficiently, e.g. a library for CG sequencing platform.

In an embodiment of the present disclosure, the first adaptor and the second adaptor are ligated to the double-stranded DNA fragment respectively at two terminals in one step.

In an embodiment of the present disclosure, the device further includes a tenth unit configured to extract the genomic DNA from a biological sample; and/or an eleventh unit configured to subject RNA to reverse transcription to obtain a reverse transcription product, in which at least part of genomic DNA and/or the reverse transcription product constitute(s) the DNA sample.

In an embodiment of the present disclosure, the eighth unit is further configured to: contact the DNA fragment ligated with the first and second adaptors respectively at two terminals with magnetic beads, to form a magnetic bead-DNA complex, in which the magnetic bead is coated with streptavidin; and expose the magnetic bead-DNA complex to a solution being of a pH value higher than 7 to obtain the single-stranded DNA fragment, thereby effectively isolating the single-stranded DNA fragment, so as to improve efficiency of library construction and reduce cost for library construction.

In an embodiment of the present disclosure, the device further includes a twelfth unit configured to screen the DNA fragment ligated with the first and second adaptors respectively at two terminals, from which the single-stranded DNA fragment is isolated thereafter. In an embodiment of the present disclosure, the DNA fragment ligated with the first and second adaptors respectively at two terminals is screened by means of contact with a probe, in which the probe is specific to a predetermined sequence. In an embodiment of the present disclosure, the predetermined sequence includes at least one exon. In an embodiment of the present disclosure, the probe is provided in a microchip array form.

In an embodiment of the present disclosure, the ninth unit is further configured to cyclize the single-stranded DNA fragment with a single-stranded nucleic acid molecule, in which the single-stranded nucleic acid molecule comprises a first region and a second region, the first region is capable of pairing with terminal nucleotides at the 5'-end and the 3'-end of the single-stranded DNA fragment, and the second region is capable of pairing with terminal nucleotides at the 5'-end or the 3'-end of the single-stranded DNA fragment, thereby effectively cyclizing the single-stranded DNA fragment with the single-stranded nucleic acid molecule.

In conclusion, the technical solution according to embodiments of the present disclosure has at least one of the following advantages.

Firstly, the technical solution according to embodiments of the present disclosure has reduced adaptor ligating steps which are prevalent to be redundant in the existing method of constructing the library for Complete Genomics sequencing platform.

In various embodiments of the present disclosure, a new method of adding different adaptors to the DNA fragment respectively at two terminals in one step is provided, instead of in respective multiple steps commonly-used in the traditional method.

In various embodiments of the present disclosure, it is also required to avoid adaptor self-connection, fragments interconnection, etc. even for simultaneously ligating two different adaptors to a DNA fragment respectively at two terminals. However, the adaptor for use in the present disclosure is designed with a unique sequence and ligated by the novel method, which prevents fragments interconnection and adaptor self-connection, improves ligating efficiency, and provides a position where the tag sequence is introduced, thereby greatly reducing steps of adaptor ligation, shortening period for adaptor ligation and significantly reducing cost.

In various embodiments of the present disclosure, this original adaptor ligation method is combined with technology for capturing nucleic acids with a probe. Upon further modifying and adjusting the traditional protocol of constructing a library for Complete Genomics sequencing platform, different adaptors are successively ligated to the DNA fragment respectively at two terminals in one step, rather than in two steps, thereby significantly shortening period for library construction and reducing corresponding cost. Moreover, a whole exome sequencing product is created successfully with a single adaptor based on the CG sequencing platform.

Therefore, in some embodiments of the present disclosure, with reference to FIG. 1, a library is constructed as the following steps:

1. fragmenting genomic nucleic acid to obtain fragments;
2. dephosphorylating a target fragment to block the 5'-end of the target fragment, so as to prevent fragments from ligating to each other;
3. end-repairing each terminal of the target fragment, resulting in paired blunt ends (indicated by 2 as shown in FIG. 1);
4. ligating the adaptor A (indicated by 3 as shown in FIG. 1) and the adaptor B (indicated by 4 as shown in FIG. 1) to the target fragment respectively at two terminals, in which the adaptor A and the adaptor B each are polynucleotides consisting of a long strand (a first strand) and a short strand (a second strand). Due to having a phosphate group at the 5'-end, the long strand can be ligated to the end-repaired fragment; while the short strand is paired with the long strand by complementary base pairing, However, the short strand will not be ligated to the end-repaired fragment because both ends of the short strand are blocking sequences;
5. adding a single-stranded nucleic acid C (indicated by 5 as shown in FIG. 1) and a single-stranded nucleic acid D (indicated by 7 as shown in FIG. 1), in which the single-stranded nucleic acid C has a tag sequence (indicated by 6 as shown in FIG. 1) and the rest part of the single-stranded nucleic acid C is paired with the long strand of the adaptor A; whilst the single-stranded nucleic acid D is paired with the long strand of the adaptor B; After annealing process, the short strand of respective adaptor, which is combined in a weak way, is removed; and the single-stranded nucleic acids C and D are complementary paired with respective long strand of the adaptor, such that the single-stranded nucleic acids C and D are ligated to the target fragment after extension and ligation.
6. amplifying a resulting product obtained in step 4 (as a template) with the single-stranded nucleic acids C and D as primers by polymerase chain reaction, thereby enriching a product with a tag sequence;
7. capturing a resulting product obtained in step 5 by hybridizing with an oligonucleotide probe, specifically including hybridizing with the probe, eluting a hybridized product, and enriching the hybridized product during which introducing a biotin modification into one of the nucleic acid strands;
8. screening the double-stranded nucleic acids after capturing by hybridization based on its length (optionally);
9. separating the screened double-stranded nucleic acid into two single-stranded nucleic acid fragments through the biotin only existing in one of the double strands of the nucleic acid;

10. cyclizing the single-stranded nucleic acid fragment and removing uncyclized single-stranded nucleic acid fragment;

It should be noted that the screening step based on the lengths of nucleic acids may be performed after other steps prior to step 9 of separating the screened double-stranded nucleic acid into two single-stranded nucleic acid fragments, depending on specific requirement for sequencing and actual size of fragments resulted from different steps. If the fragments resulted from different steps always meet the length requirement, step 8 may be omitted.

The whole exome sequencing can be achieve by introducing the step 7.

In an embodiment of the present disclosure, after end blocking treatment by means of dephosphorylation in the steps 2 and 3, the target nucleic acid fragment become to be a fragment having two blocked terminals each of which is a pair of blunt end, thus preventing the fragments from ligating to each other completely, and ensuring high unitization of fragments prior to ligation.

In an embodiment of the present disclosure, the adaptor used herein is designed to be introduced a phosphate group in the long strand at the 5'-end, as well as introduced blocking sequences in the long strand at the 3'-end and the short strand at both ends. Due to the blocking sequences, these blocked ends are incapable of ligating to the target nucleic acid fragment or other adaptors added simultaneously, such that it is guaranteed that the adaptor is ligated to the 3'-end of the target fragment precisely and only with the 5'-end when ligating adaptors in the step 4, thereby effectively preventing the adaptors from ligating to each other, allowing for ligating different adaptors at the same time and guaranteeing ligating efficiency.

In some embodiments of the present disclosure, the adaptor consisting of a long strand and a short strand as described previously is unitized in such a way that the short strand will be separated from the long strand under a relative moderate temperature due to unstable combination with a few of complementary paired bases therebetween; after slow annealing, the long strand is paired with the single-stranded nucleic acid C or D which has better ability of complementary pairing due to the longer sequence; and a recognition tag is provided at the same time by introducing a tag sequence in the single-stranded nucleic acid C. With the adaptor designed in the above ways merely requiring a moderate condition for reaction, fragment replacement, ligation and extension can be conducted in one step (eg. as shown in the step 5) by means of adjusting a reaction system, a reaction period and reaction orders as appropriated, resulting in simple operations and rapid reaction, which greatly reduces period for processing.

In various embodiments of the present disclosure, two different adaptors are ligated to the DNA fragments respectively at two terminals within three steps (i.e., adaptor ligation, nick translation and polymerase chain reaction), instead of the traditional five steps, which greatly decreases operations, and reduces various reagents used for extra two steps, thereby saving a large amount of time and cost.

According to various embodiments of the present disclosure, not only specific steps for adaptor ligation are fully changed, but also the traditional protocol of library construction for CG sequencing platform has been subversively altered to provide a novel library consisting of single-stranded nucleic acids (indicated by 8 as shown in FIG. 1), such that two different adaptors are ligated to the DNA fragments respectively at two terminals in one step, simplified from two times of adaptor ligation in the tradition protocol, thereby reducing times of polymerase chain reactions and improving sequencing quality. More importantly, steps simplification allows the period for library construction to be shortened by 3 to 4 days, resulting in significant reduction in cost, which has a huge advantage as compared with the traditional protocol for library construction.

According to various embodiments of the present disclosure, a high efficient protocol of library construction for human whole exome for CG sequencing platform is developed and provided successfully by modifying and supplementing the tradition protocol of library construction for CG sequencing platform and combining the novel method of adaptor ligation described above. In addition, it is also provided for the first time a new product for sequencing human whole exome on CG sequencing platform, thus achieving a breakthrough of whole exome sequencing on CG sequencing platform from nothing.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang PT), Molecular Cloning: A Laboratory Manual, 3rd Ed., Science Press) or in accordance with the product instructions. If the manufacturers of reagents or instruments are not specified, the reagents or instruments may be commercially available.

General Method

With reference to FIG. 1, in an embodiment of the present disclosure, a library is constructed in accordance with the following steps:

1. fragmenting genomic nucleic acid to obtain fragments;

2. dephosphorylating a target fragment to block the 5'-end of the target fragment, so as to prevent fragments from ligating to each other;

3. end-repairing each terminal of the target fragment, resulting in paired blunt ends (indicated by 2 as shown in FIG. 1);

4. ligating the adaptor A (indicated by 3 as shown in FIG. 1) and the adaptor B (indicated by 4 as shown in FIG. 1) to the target fragment respectively at two terminals, in which the adaptor A and the adaptor B each are polynucleotides consisting of a long strand (a first strand) and a short strand (a second strand). Due to having a phosphate group at the 5'-end, the long strand can be ligated to the end-repaired fragment; while the short strand is paired with the long strand by complementary base pairing, However, the short strand will not be ligated to the end-repaired fragment because of a blocked end;

5. adding a single-stranded nucleic acid C (indicated by 5 as shown in FIG. 1) and a single-stranded nucleic acid D (indicated by 7 as shown in FIG. 1), in which the single-stranded nucleic acid C has a tag sequence (indicated by 6 as shown in FIG. 1) and the rest part of the single-stranded nucleic acid C is paired with the long strand of the adaptor A; whilst the single-stranded nucleic acid D is paired with the long strand of the adaptor B; After annealing process, the short strand of respective adaptor, which is combined in a weak way, is removed; and the single-stranded nucleic acids C and D are complementary paired with respective long strand of the adaptor, such that the single-stranded nucleic acids C and D are ligated to the target fragment after extension and ligation.

6. amplifying a resulting product obtained in step 4 (as a template) with the single-stranded nucleic acids C and D as primers by polymerase chain reaction, thereby enriching a product with a tag sequence;

7. capturing a resulting product obtained in step 5 by hybridizing with an oligonucleotide probe, specifically including hybridizing with the probe, eluting a hybridized product, and enriching the hybridized product during which introducing a biotin modification into one of the nucleic acid strands;

8. screening the double-stranded nucleic acids after capturing by hybridization based on its length (optionally);

9. separating the screened double-stranded nucleic acid into two single-stranded nucleic acid fragments through the biotin only existing in one of the double strands of the nucleic acid;

10. cyclizing the single-stranded nucleic acid fragment and removing uncyclized single-stranded nucleic acid fragment;

It should be noted that the screening step based on the lengths of nucleic acids may be performed after other steps prior to step 9 of separating the screened double-stranded nucleic acid into two single-stranded nucleic acid fragments, depending on specific requirement for sequencing and actual size of fragments resulted from different steps. If the fragments resulted from different steps always meet the length requirement, step 8 may be omitted.

The whole exome sequencing can be achieve by introducing the step 7

Example 1

1. Genomic DNA Fragmentation

The genomic DNA can be fragmented in several ways, such as physical ultrasonication and enzyme digestion, both of which has well-established procedures commercially available. In the present example, the physical ultrasonication was used for fragmentation.

To a 96-well PCR plate, one polytetrafluoroethylene wire, 1 µg genomics DNA and Tris-EDTA (TE) buffer or nuclease-free water were added up to 80 µl for each well. After sealed with a perseverative film, the 96-well PCR plate was placed onto E220 ultrasonicator for fragmentation under conditions as below.

| Duty Cycle | 20% |
| Intensity | 5 |
| Cycles per Burst | 200 |
| Fragmenting Duration | 60 s, 5 times |

2. Selection of Fragmented Genomic DNA

The fragmented genomic DNA can be selected out by magnetic beads purification or gel-recovery. In the present example, the magnetic beads purification was used for selection.

The fragmented genomic DNA was mixed with 80 µl Ampure XP magnetic beads to be uniform, followed by still standing f for 7 min to 15 min. The first supernatant collected after placed onto magnetic separator for a while was mixed with 40 µl fresh Ampure XP magnetic beads to be uniform, followed by still standing f for 7 min to 15 min. The second supernatant collected after placed onto magnetic separator for another while was washed with 75% ethanol twice. After dried, resultant was mixed with 50 µl TE buffer or nuclease-free water to be uniform followed by still standing f for 7 min to 15 min, for dissolving recovered product.

3. Dephosphorylation

A first reaction solution was formulated as below.

| 10x NEB buffer 2 | 6 µl |
| Shrimp alkaline phosphatase (1 U/µl) | 6 µl |
| Total volume | 12 µl |

The recovered product obtained in the previous step 2 was mixed with 12 µl of the first reaction solution to be uniform for reactions under conditions as below. The resulting product generated was directly used for the subsequent step. The step of cooling to 4° C. at a rate of 0.1° C./s is not obligatory; and it does not need to accurately control duration for reaction. Hereinafter inclusive.

| 37° C. | 45 min |
| 65° C. | 10 min | cooling to 4° C. at a rate of 0.1° C./s

4. End-Repairing

A second reaction solution was formulated as below to be uniform.

| Nuclease-free water | 12.2 µl |
| 10x NEB buffer2 | 1.8 µl |
| 0.1M triphosadenine | 0.8 µl |
| 25 mM deoxyribonucleoside triphosphate | 0.8 µl |
| Bovine Serum Albumin | 0.4 µl |
| T4 DNA polymerase (3 U/µl) | 2 µl |
| Total volume | 18 µl |

The dephosphorylated product obtained in the previous step 3 was mixed with the second reaction solution to be uniform, followed by incubation at 12° C. for 20 min, purification with 80 µl PEG 32 magnetic beads, and recovery by dissolving in 40 µl TE buffer. The resulting product can be purified in several ways, i.e., using magnetic beads, passing through a column, running gel and isolating target product therefrom, etc., which are used exchangeable. In the present example, the resulting product was purified with magnetic beads, unless otherwise specified.

5. Adaptors A and B Ligation

In the present example, the adaptors used have respective sequence as below. It should be note that the sequence is written from the 5'-end to the 3'-end in a left-to-right manner; "II" means a group therein is a modifying group for a terminal nucleotide, or a terminal nucleotide therein has been modified; "phos" indicates phosphorylation; "dd" indicates dideoxy; and "bio" represents biotin.

```
Adaptor A:
Long strand:
/Phos/GGCTCCGTCGAAGCCCGACG/ddC/

Short strand:
GCTTCGACGGAGC/ddC/
```

```
Adaptor B:
Long strand:
/phos/ACGTCGGGGCCAAGCGGTCGT/ddC/

Short strand:
TTGGCCCCGGCT/-ddT/.
```

A third reaction solution was formulated as below to be uniform.

| Nuclease-free water | 11.1 µl |
|---|---|
| 5 µM adaptor A | 1.85 µl |
| 5 µM adaptor B | 1.85 µl |
| Total volume | 14.8 µl |

A fourth reaction solution was formulated as below to be uniform.

| Nuclease-free water | 25 µl |
|---|---|
| 10XT4 DNA ligating buffer (Enzymatics, L6030-HC-L) | 3 µl |
| T4 DNA ligase (quick) (600 U/µl) (Enzymatics, L6030-HC-L) | 2 µl |
| Total volume | 30 µl |

The end-repaired product obtained in the previous step 4 was mixed with the third reaction solution and then the fourth reaction solution to be uniform, followed by incubation at 20° C. for 20 min, purification with 100 µl Ampure XP magnetic beads, and recovery by dissolving in 40 µl TE buffer.

Figure 2:
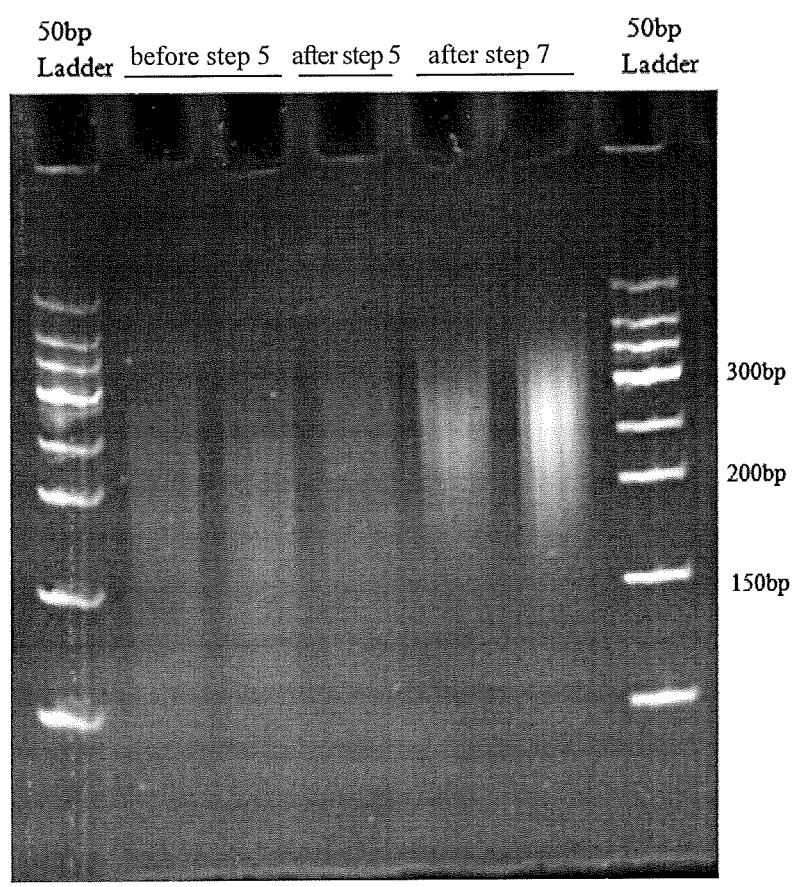
FIG. 2 is an electrophoretogram in an embodiment of the present disclosure.

The adaptor A and the adaptor B were ligated to the target fragment after this step. FIG. 2 has shown an electrophoretogram before and after adaptor ligation. As can be seen from FIG. 2, the DNA fragment is of an obvious longer size after adaptor ligation in step 5, indicating that the current method according to present example is very successful. In particularly, effects of screening and enriching are more obvious with more intensive band after polymerase chain reaction in step 5.

6. Binding with Single-Stranded Nucleic Acids C and D the single-stranded nucleic acid C:
/phos/AGACAAGCTCxxxxxxxxxxGATCGGGCTTC-GACGGAG ("x" located intermediately refers to a tag sequence consisting of exchangeable nucleotides)

the single-stranded nucleic acid D: /bio/TCCTAAGAC-CGCTTGGCCCCGA.

A fifth reaction solution was formulated as below to be uniform

| Nuclease-free water | 19.88 µl |
|---|---|
| 10x Taq butter | 8 µl |
| 0.1M triphosadenine | 0.8 µl |
| 25 mM deoxyribonucleoside triphosphate | 0.32 µl |
| 20 µM single-stranded nucleic acid D | 0.5 µl |
| Total volume | 30 µl |

A sixth reaction solution was formulated as below to be uniform.

| Nuclease-free water | 0.4 µl |
|---|---|
| 10x Taq buffer | 0.4 µl |
| T4 DNA ligase (600 U/µl) | 4.8 µl |
| Taq polymerase (5 U/µl) | 2.4 µl |
| Total volume | 8 µl |

The recovered product ligated with the adaptor A and the adaptor B respectively at two terminals were mixed with 1 µl of single-stranded nucleic acid C (10 µM) to be uniform, which were then incubated at 65° C. for 5 min and cooled to 37° C. at a rate of 0.1° C./s, at which temperature 8 µl fifth reaction solution was further added for another incubation for 20 min.

The resulting product thus obtained was purified with 96 µl Ampure XP magnetic beads, and recovery by dissolving in 25 µl TE buffer.

7. Polymerase Chain Reaction

A seventh reaction solution was formulated as below to be uniform.

| Nuclease-free water | 15.5 µl |
|---|---|
| 10x PfuTurbo Cx buffer (Agilent, 01.Agilent.600414) | 50.0 µl |
| PfuTurbo Cx Hot-start DNA polymerase (2.5 U/µl) (Agilent, 01.Agilent.600414) | 2 µl |
| 20 µM single-stranded nucleic acid D | 2.5 µl |
| 10 µM single-stranded nucleic acid C | 5.0 µl |
| Total volume | 75.0 µl |

After dissolved in nuclease-free water or TE buffer up to 25 µl, 30 ng to 40 ng resulting product with the single-stranded nucleic acid C and single-stranded nucleic acid D was mixed with seventh reaction solution to be uniform, followed by reaction under the following conditions.

| 95° C. | 3 min |
|---|---|
| 95° C. | 30 s |
| 56° C. | 30 s |
| 72° C. | 90 s |
| 68° C. | 7 min | cooling to 4° C. at a rate of 0.1° C./s

After the reaction, the amplified product was purified with 120 µl Ampure XP magnetic beads, followed by recovery by dissolving in 25 µl nuclease-free water.

8. Capturing by Hybridization

An eighth reaction solution was formulated as below.

| nuclease-free water | 3.4 µl |
|---|---|
| SureSelect Block #1 (Agilent) | 2.5 µl |
| SureSelect Block #2 (Agilent) | 2.5 µl |
| Blocking sequence for Adaptor A | 0.3 µl |
| Blocking sequence for Adaptor B | 0.3 µl |
| Total volume | 9 µl |

After concentration and evaporation, 500 ng to 1 µg of the recovered product obtained after amplification was mixed with the eighth reaction solution to be uniform, followed by incubated at 95° C. for 5 min, and then held at 65° C. (first reaction system).

A ninth reaction solution was formulated as below.

| SureSelect Hyb #1 (Agilent) | 8.3 μl |
| SureSelect Hyb #2 (Agilent) | 0.3 μl |
| SureSelect Hyb #3 (Agilent) | 3.3 μl |
| SureSelect Hyb #4 (Agilent) | 4.3 μl |
| Total volume | 16.3 μl |

The ninth reaction solution was then added into the first reaction system for continue incubation at 65° C. (second reaction system).

A tenth reaction solution was formulated as below.

| Nuclease-free water | 1 μl |
| SureSelect RNase Block (Agilent) | 1 μl |
| SureSelect Oligo Capture Library | 5 μl |
| Total volume | 7 μl |

The tenth reaction solution was added into the second reaction system, followed by incubation at 65° C. for 20 h to 24 h (third reaction system).

After the reaction, the resulting product in the third reaction system was contacted with magnetic beads coated with streptavidin, after which the magnetic beads were dissolved in 50 μl nuclease-free water.

An eleventh reaction solution was formulated as below.

| Nuclease-free water | 31 μl |
| 10x PfuTurbo Cx buffer (Agilent, 01.Agilent.600414) | 100.0 μl |
| PfuTurbo Cx Hot-start DNA polymerase (Agilent, 01.Agilent.600414) | 4 μl |
| 20 μM single-stranded nucleic acid D (modified with biotin) | 5 μl |
| 10 μM single-stranded nucleic acid C | 10 μl |
| Total volume | 150 μl |

The magnetic beads dissolved in nuclease-free water were then mixed with the eleventh reaction solution followed by reactions under the following conditions.

| 95° C. | 3 min |
| 95° C. | 30 s |
| 56° C. | 30 s |
| 72° C. | 90 s |
| 68° C. | 7 min | cooling to 4° C. in a rate of 0.1° C./s

After the reaction, the resulting product was purified with 240 μl Ampure XP magnetic beads.

9. Separating the Screened Double-Stranded Nucleic Acid into Two Single-Stranded Nucleic Acid Fragments The resulting magnetic bead-DNA complex obtained in the previous step 8 was exposed to 0.1 M sodium hydroxide, so as to isolate the single-stranded nucleic acid fragment which does not contain the biotin and thus does not bind with the magnetic beads coated with streptavidin, followed by addition of acidic buffer for neutralization. After the neutralization, the total volume was 112 μl.

10. Cyclization of the Single-Stranded Nucleic Acid Fragment

A twelfth reaction solution was formulated as below, in which the single-stranded nucleic acid E has a sequence complementary for two ends of the single-stranded nucleic acid fragment obtained in the previous step 9 for connection.

The single-stranded nucleic acid E has a sequence of TCGAGCTTGTCTTCCTAAGACCGC (SEQ ID NO:8).

| Nuclease-free water | 43 μl |
| single-stranded nucleic acid E | 20 μl |
| Total volume | 63 μl |

The twelfth reaction solution was added with the single-stranded nucleic acid fragment obtained in the previous step 9 and mixed to be uniform (fourth reaction system).

A thirteenth reaction solution was formulated as below.

| Nuclease-free water | 153.3 μl |
| 10xTA buffer (Epicentre) | 35 μl |
| 100 mM triphosadenine | 3.5 μl |
| T4 DNA ligase (quick) (600 U/μl) (Enzymatics, L6030-HC-L) | 1.2 μl |
| Total volume | 175 μl |

The thirteenth system was added into the fourth reaction system and mixed to be uniform, followed by incubation at 37° C. for 1.5 h.

11. Treatment with Exonuclease 1 and Exonuclease 2

A fourteenth reaction solution was formulated as below.

| Nuclease-free water | 1.5 μl |
| 10xTA buffer (Epicentre) | 3.7 μl |
| Exonuclease 1 (20 U/μl) (NEB, M0293S) | 11.1 μl |
| Exonuclease 3 (100 U/μl) (NEB, M0206S) | 7.4 μl |
| Total volume | 23.7 μl |

23.7 μl of the fourteenth reaction solution was mixed with the resulting cyclization product in the previous step 9 to be uniform, followed by still standing at 37° C. for 1.5 h for incubation, which was then added with 15.4 μl mM ethylenediamine tetraacetic acid (EDTA). The resulting product thus obtained was purified with 500 μl PEG32 magnetic beads and redissolved in 40 μl to 80 μl nuclease-free water/TE buffer, thereby obtaining a final product.

The final products obtained as illustrated in the present example have concentrations and total amounts as follows:

| | Concentration (ng/μl) | Amount (ng) |
|---|---|---|
| Final product 1 | 2.72 | 108.8 |
| Final product 2 | 2.12 | 84.8 |
| Final product 3 | 4.26 | 170.4 |
| Final product 4 | 1.46 | 58.4 |
| Final product 5 | 3.06 | 122.4 |
| Final product 6 | 1.73 | 69.2 |

Figure 3:
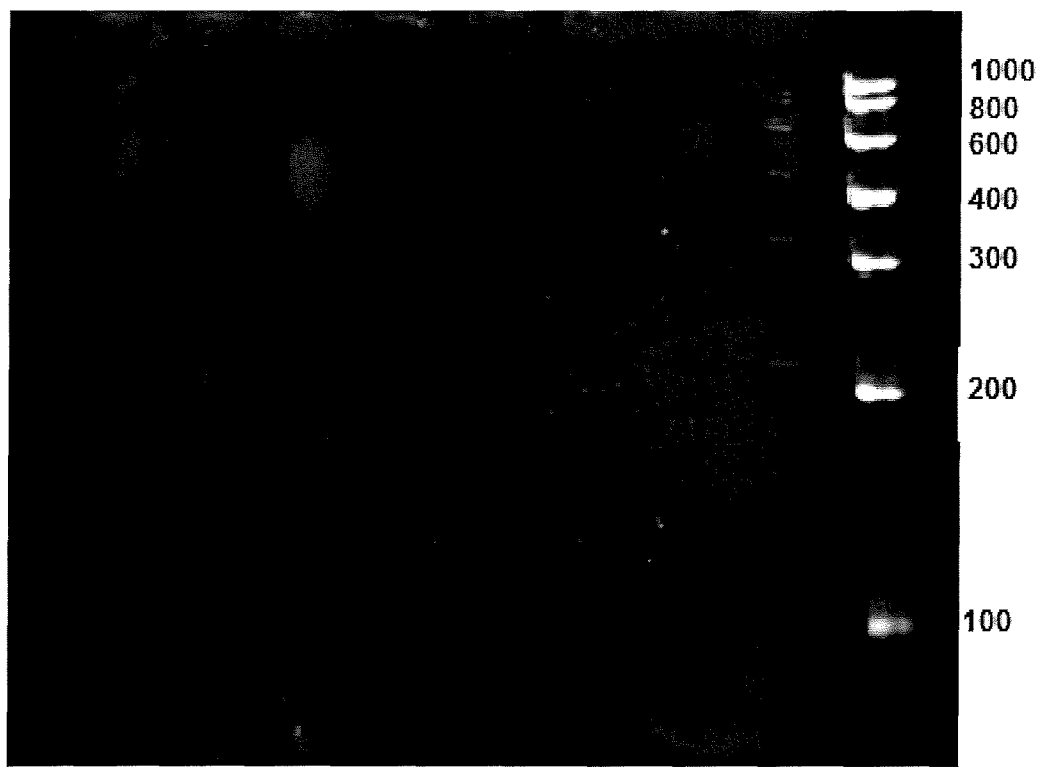
FIG. 3 is an electrophoretogram in an embodiment of the present disclosure.

An electrophoretic result is shown in FIG. 3, which is an electrophoretogram for the final products from the step 11 by 6% polyacrylamide modified gel electrophoresis. As shown in FIG. 3, the final products 1, 3 and 5 have been subjected length screening via gel electrophoresis after hybridization; while the final products 2, 4 and 6 have not subjected to length screening. As can be seen from FIG. 3, the final products after subjected to length screening will have more intensive size. All of the final products, regardless subjected to or not to length screening, can be sequenced successfully, thus indicating that this solution of the present disclosure is fully successful

INDUSTRIAL APPLICABILITY

According to embodiments of the present disclosure, the isolated oligonucleotide can be effectively used as an adaptor for library construction; besides the method provided herein can ligate different adaptors to a nucleic acid fragment respectively at two terminals at the same time, which avoids adaptors from interconnecting to each other, thus improving ligating efficiency and reducing economic and time cost for library construction.

Reference throughout this specification to "an embodiment," "some embodiments," "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An isolated oligonucleotide, comprising a first strand and a second strand, wherein
   a first terminal nucleotide at the 5'-end of the first strand has a phosphate group, and a second terminal nucleotide at the 3'-end of the first strand is dideoxynucleotide; and
   a third terminal nucleotide at the 5'-end of the second strand has no phosphate group, and a fourth terminal nucleotide at the 3'-end of the second strand is dideoxynucleotide,
   wherein the first strand is of a length longer than that of the second strand, and a double-stranded structure is formed between the first strand and the second strand.

2. The isolated oligonucleotide according to claim 1, wherein the number of nucleotides mismatched between the second strand and the first strand is no more than 3.

3. The isolated oligonucleotide according to claim 1, comprising:
   a first overhang, located at the 3'-end of the first strand; or
   a first overhang located at the 3'-end of the first strand and a second overhang located at the 5'-end of the second strand.

4. The isolated oligonucleotide according to claim 1, wherein the length of the first strand is about 20 nt to about 25 nt.

5. The isolated oligonucleotide according to claim 1, wherein
   the first strand has a sequence of 5'GGCTCCGTC-GAAGCCCGACGC3', and
   the second strand has a sequence of 5'CTTCGACG-GAGCC3';
   or
   the first strand has a sequence of 5'ACGTCGGGGC-CAAGCGGTCGTC3', and
   the second strand has a sequence of 5'TTGGCCCCG-GCTT3'.

6. A kit, comprising:
   a first adaptor and a second adaptor each being the isolated oligonucleotide according to claim 1,
   wherein the first adaptor is different from the second adaptor.

7. The kit according to claim 6, further comprising:
   a first single-stranded DNA capable of pairing with a first strand of the first adaptor to form a first double-stranded structure; and
   a second single-stranded DNA capable of pairing with a first strand of the second adaptor to form a second double-stranded structure.

8. The kit according to claim 7, further comprising:
   a first primer being the same as one of the first single-stranded DNA and the second single-stranded DNA; and
   a second primer having additional biotin at the 5'-end as compared to the other one of the first single-stranded DNA and the second single-stranded DNA.

9. The kit according to claim 8, wherein
   the first strand of the first adaptor has a sequence of 5'GGCTCCGTCGAAGCCCGACGC3';

a second strand of the first adaptor has a sequence of 5'CTTCGACGGAGCC3';

the first strand of the second adaptor has a sequence of 5'ACGTCGGGGCCAAGCGGTCGTC3';

a second strand of the second adaptor has a sequence of 5'TTGGCCCCGGCTT3';

the first single-stranded DNA has a sequence of 5'AGACAAGCTC(N)$_m$GATCGGGCTTCGACGGAG3', wherein (N)$_m$ represents a tag sequence being of a length of m nucleotides, where m is an integer ranging from 4 to 10, and N represents adenine (A), thymine (T), guanine (G) or cytosine (C); and the second single-stranded DNA has a sequence of 5'TCCTAAGACCGCTTGGCCCCG3'.

10. A method for adding adaptors, comprising a first adaptor and a second adaptor, to a double-stranded DNA fragment respectively at two terminals, each of which comprises paired blunt ends without any phosphate group, the method comprising:
ligating the first adaptor and the second adaptor to the double-stranded DNA fragment respectively at two terminals, to obtain a first ligated product,
wherein the first adaptor is different from the second adaptor; and
the first adaptor and the second adaptor each are the isolated oligonucleotide according to claim 1;
replacing a second strand of the first adaptor by a first single-stranded DNA and replacing a second strand of the second adaptor by a second single-stranded DNA, wherein the first single-stranded DNA is capable of specifically pairing with a first strand of the first adaptor to form a first double-stranded structure, and the second single-stranded DNA is capable of specifically pairing with a first strand of the second adaptor to form a second double-stranded structure;
connecting the first single-stranded DNA and the second single-stranded DNA to the double-stranded DNA fragment respectively at two terminals to obtain a second ligated product, and
amplifying the second ligated product with a first primer and a second primer to obtain an amplified product, wherein
the amplified product is a DNA fragment ligated with the first and second adaptors respectively at two terminals,
the first primer contains the same sequence as one of the first single-stranded DNA and the second single-stranded DNA, and
the second primer contains the same sequence as the other one of the first single-stranded DNA and the second single-stranded DNA and contains additional biotin at the 5'-end as compared to the other one of the first single-stranded DNA and the second single-stranded DNA.

11. The method according to claim 10, wherein the first adaptor and the second adaptor are ligated to the double-stranded DNA fragment respectively at two terminals in one step.

12. The method according to claim 10, wherein
the first double-stranded structure is of a length longer than that of a third double-stranded structure formed with the first strand of the first adaptor and a second strand of the first adaptor; and
the second double-stranded structure is of a length longer than that of a fourth double-stranded structure formed with the first strand of the second adaptor and a second strand of the second adaptor.

13. The method according to claim 10, wherein the second strand of the first adaptor and the second strand of the second adaptor are replaced respectively by the first single-stranded DNA and the second single-stranded DNA by means of thermal denaturation-annealing.

14. The method according to claim 10, wherein the first single-stranded DNA and the second stranded DNA are connected to the double-stranded DNA fragment respectively at two terminals by means of nick translation.

15. A method of constructing a library for sequencing a double-stranded DNA fragment with two terminals, each of which comprises paired blunt ends without any phosphate group, the method comprising:
ligating the first adaptor and the second adaptor to the double-stranded DNA respectively at two terminals by the method according to claim 10, to obtain a DNA fragment ligated with the first and second adaptors respectively at two terminals;
separating the DNA fragment ligated with the first and second adaptors respectively at two terminals into single-stranded DNA fragments; and
cyclizing the single-stranded DNA fragment to obtain a single-stranded DNA loop,
wherein the single-stranded DNA loop constitutes the library for sequencing the double-stranded DNA fragment with two terminals.

16. The method according to claim 15, wherein separating the DNA fragment ligated with the first and second adaptors respectively at two terminals into single-stranded DNA fragments further comprises:
contacting the DNA fragment ligated with the first and second adaptors respectively at two terminals with magnetic beads to form a magnetic bead-DNA complex, wherein the magnetic bead is coated with streptavidin; and
exposing the magnetic bead-DNA complex to a solution being of a pH value higher than 7 to obtain the single-stranded DNA fragment.

17. The method according to claim 16, wherein the solution being of the pH value higher than 7 is a sodium hydroxide solution.

18. The method according to claim 15, wherein the single-stranded DNA fragment is isolated from the DNA fragment ligated with the first and second adaptors respectively at two terminals, which has been screened in advance.

19. The method according to claim 18, wherein
the DNA fragment ligated with the first and second adaptors respectively at two terminals is screened by means of contact with a probe, wherein the probe is specific to a predetermined sequence.

20. The method according to claim 15, wherein the single-stranded DNA fragment is cyclized with a single-stranded nucleic acid molecule,
wherein the single-stranded nucleic acid molecule comprises a first region and a second region,
the first region is capable of pairing with terminal nucleotides at the 5'-end and the 3'-end of the single-stranded DNA fragment, and
the second region is capable of pairing with terminal nucleotides at the 5'-end or the 3'-end of the single-stranded DNA fragment
wherein the first region is adjacent connected to the second region.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: first strand of first adaptor

<400> SEQUENCE: 1
ggctccgtcg aagcccgacg c                                              21

<210> SEQ ID NO 2
<211> LENGTH: 13
<212> TYPE: DNA
<213> ORGANISM: Artificial
<220> FEATURE:
<223> OTHER INFORMATION: second strand of first adaptor

<400> SEQUENCE: 2
cttcgacgga gcc                                                       13

<210> SEQ ID NO 3
<211> LENGTH: 22
<212> TYPE: DNA
<213> ORGANISM: Artificial
<220> FEATURE:
<223> OTHER INFORMATION: first strand of second adaptor

<400> SEQUENCE: 3
acgtcggggc caagcggtcg tc                                             22

<210> SEQ ID NO 4
<211> LENGTH: 13
<212> TYPE: DNA
<213> ORGANISM: Artificial
<220> FEATURE:
<223> OTHER INFORMATION: second strand of second adaptor

<400> SEQUENCE: 4
ttggccccgg ctt                                                       13

<210> SEQ ID NO 5
<211> LENGTH: 21
<212> TYPE: DNA
<213> ORGANISM: Artificial
<220> FEATURE:
```

```
<223> OTHER INFORMATION: second single-stranded DNA

<400> SEQUENCE: 5
tcctaagacc gcttggcccc g                                            21

<210> SEQ ID NO 6
<211> LENGTH: 12
<212> TYPE: DNA
<213> ORGANISM: Artificial
<220> FEATURE:
<223> OTHER INFORMATION: first region of single-stranded nucleic acid

<400> SEQUENCE: 6
tcgagcttgt ct                                                      12

<210> SEQ ID NO 7
<211> LENGTH: 12
<212> TYPE: DNA
<213> ORGANISM: Artificial
<220> FEATURE:
<223> OTHER INFORMATION: second region of single-stranded nucleic acid

<400> SEQUENCE: 7
tcctaagacc gc                                                      12

<210> SEQ ID NO 8
<211> LENGTH: 24
<212> TYPE: DNA
<213> ORGANISM: Artificial
<220> FEATURE:
<223> OTHER INFORMATION: single-stranded nucleic acid E

<400> SEQUENCE: 8
tcgagcttgt cttcctaaga ccgc                                         24
```